US011154507B2

(12) United States Patent
Hiraoka

(10) Patent No.: US 11,154,507 B2
(45) Date of Patent: Oct. 26, 2021

(54) FREEZE-DRIED ARIPIPRAZOLE FORMULATION

(75) Inventor: Shogo Hiraoka, Osaka (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 14/124,459

(22) PCT Filed: Jun. 7, 2012

(86) PCT No.: PCT/JP2012/065180
§ 371 (c)(1),
(2), (4) Date: Dec. 6, 2013

(87) PCT Pub. No.: WO2012/169662
PCT Pub. Date: Dec. 13, 2012

(65) Prior Publication Data
US 2014/0112993 A1    Apr. 24, 2014

Related U.S. Application Data

(60) Provisional application No. 61/494,088, filed on Jun. 7, 2011.

(51) Int. Cl.
A61K 9/19        (2006.01)
A61K 9/16        (2006.01)
A61K 31/496      (2006.01)

(52) U.S. Cl.
CPC .............. *A61K 9/19* (2013.01); *A61K 9/1623* (2013.01); *A61K 9/1652* (2013.01); *A61K 31/496* (2013.01)

(58) Field of Classification Search
None
See application file for complete search history.

(56) References Cited

U.S. PATENT DOCUMENTS

| | | | |
|---|---|---|---|
| 5,006,528 A | 4/1991 | Oshiro et al. | |
| 5,719,123 A | 2/1998 | Morley et al. | |
| 6,977,257 B2 | 12/2005 | Parab et al. | |
| 2002/0193438 A1 | 12/2002 | Parab et al. | |
| 2005/0032811 A1 | 2/2005 | Brown | |
| 2005/0152981 A1* | 7/2005 | Gleeson | B01D 9/0009 424/489 |
| 2007/0035051 A1 | 2/2007 | Darnton et al. | |
| 2007/0148100 A1* | 6/2007 | Jenkins | A61K 9/0019 424/46 |

FOREIGN PATENT DOCUMENTS

| | | |
|---|---|---|
| CN | 1512884 A | 7/2004 |
| JP | 2007/047805 A | 2/2007 |
| JP | 2009-508859 A | 3/2009 |
| WO | WO 95/13814 A1 | 5/1995 |
| WO | WO 99/12549 A2 | 3/1999 |
| WO | WO 03/026659 A1 | 4/2003 |
| WO | WO 2005/041937 A2 | 5/2005 |
| WO | WO 2005/041970 A1 | 5/2005 |
| WO | WO 2007/035348 A2 | 3/2007 |
| WO | WO 2009/017250 A1 | 2/2009 |

OTHER PUBLICATIONS

International Search Report from the European Patent Office for International Application No. PCT/JP2012/065180, dated Aug. 9, 2012.
Written Opinion of the International Searching Authority from the European Patent Office for International Application No. PCT/JP2012/065180, dated Aug. 9, 2012.
Rogers et al.; "Enhanced Aqueous Dissolution of a Poorly Water Soluble Drug by Novel Particle Engineering Technology: Spray-Freezing Into Liquid With Atmospheric Freeze-Drying", Pharmaceutical Research, vol. 20, No. 3, pp. 485-493, (2003).
Hu et al.; "Improvement of Dissolution Rates of Poorly Water Soluble Apis Using Novel Spray Freezing Into Liquid Technology", Pharmaceutical Research, vol. 19, No. 9, pp. 1278-1284, (2002).
Maa et al.; "Stabilization of Alum-Adjuvanted Vaccine Dry Powder Formulations: Mechanism and Application", Journal of Pharmaceutical Sciences, vol. 92, No. 2, pp. 319-332, (2003).
Cohen, Z., "Production Potential of Eicosapentaenoic Acid by *Monodus subterraneus*," *Journal of the American Oil Chemist's Society*, vol. 71, No. 9, 1994, pp. 941-945.
Tan, C.K. et al., "Screening of diatoms for heterotrophic eicosapentaenoic acid production," *Journal of Applied Psychology*, vol. 8, 1996, pp. 59-64.
Vazhappilly, R. et al., "Eicosapentaenoic Acid and Docosahexaenoic Acid Production Potential of Microalgae and Their Heterotrophic Growth," *Journal of the American Oil Chemist's Society*, vol. 75, No. 3, 1998, pp. 393-397.
Wan, Zhi-You et al., "Heterotrophic production of eicosapentaenoic acid by rnicroalgae," *Biotechnology Advances*, Elsevier, vol. 21, No. 4, 2003, pp. 273-294.
"Introduction to Pharmacy of Chinese Traditional Medicine", Jan. 31, 2001, pp. 51.
"Process & Machine of Grinding for Cement Industry", Dec. 31, 1992, pp. 100.
Office Action for corresponding JP Application No. 2013-554727 dated Mar. 15, 2016.

(Continued)

*Primary Examiner* — Patricia Duffy
*Assistant Examiner* — Garen Gotfredson
(74) *Attorney, Agent, or Firm* — Finnegan, Henderson, Farabow, Garrett & Dunner, LLP

(57) ABSTRACT

An object of the present invention is to provide a freeze-dried aripiprazole powder formulation that exhibits good dispersibility and is easily dispersed into a homogenous suspension when reconstituted with water. The present invention provides a freeze-dried aripiprazole formulation obtained by a process comprising the steps of spraying for freezing an aripiprazole suspension containing (I) aripiprazole, (II) a vehicle for the aripiprazole, and (III) water for injection, and drying.

19 Claims, 6 Drawing Sheets

(56) References Cited

OTHER PUBLICATIONS

Abdelbary, Aly A. et al., "Comparative In vivo Evaluation of Aripiprazole Coprecipitate, Nanoparticles and Marketed Tablets in Healthy Human Volunteers and In vitro-In vivo Correlation," Current Trends in Biotechnology and Pharmacy, vol. 5 (4), pp. 1397-1409 Oct. 2011.
Abdul-Fattah, Ahmed M. et al., "Dying Process Methods for Biopharmaceutical Products: An Overview," Formulation and Process Development Strategies for Manufacturing Biopharmaceutics, 2010, pp. 705-738.
Bauer, Kurt H. et al., Pharmazeutische Technologie, $5^{th}$ edition; pp. 98-101 and 127-128, 1997.
Claussen, I.C. et al., "Atmospheric Freeze Drying—A Review," Drying Technology, vol. 25(6), 2007, pp. 957-967.
Communication of a Notice of Opposition in corresponding EP Patent No. 2717859 dated Jun. 8, 2017.
Hauer, B. et al., Pharmazeutische Technologie, $2^{nd}$ edition, 1991, pp. 244-247.
Maa, Yuh-Fun et al., "Spray Freeze-drying of Biopharmaceuticals: Applications and Stability Considerations," Lyophilization of Biopharmaceuticals, 2004, pp. 519-561.
Manual for Design and Selection of Dedusting Apparatus System and Device, Chemical Industry Press, 2003, p. 25, paragraph 2.
Traditional Chinese Medicine Pharmaceutics, 2007, vol. 2, p. 481.
Traditional Chinese Medicine Pharmaceutics, 2008, p. 223.
Office Action dated Feb. 6, 2020, for corresponding Chinese Patent Application No. 201610937357.1.
Office Action dated Apr. 7, 2020, for corresponding Chinese Patent Application No. 201810450421.2.

* cited by examiner

FREEZE-DRIED ARIPIPRAZOLE FORMULATION

This application claims priority to U.S. provisional application Ser. No. 61/494,088, filed Jun. 7, 2011, entitled "FREEZE-DRIED FORMULATION". The disclosure of the above referenced application is incorporated by reference herein in its entirety.

The present invention relates to a freeze-dried formulation containing aripiprazole.

TECHNICAL FIELD

Background Art

Background of the Invention

U.S. Pat. No. 5,006,528 (Oshiro et al.) discloses 7-[(4-phenylpiperazino)-butoxy]carbostyrils, which include aripiprazole, as dopaminergic neurotransmitter antagonists. Aripiprazole is an atypical antipsychotic agent useful in treating schizophrenia and has the following structure.

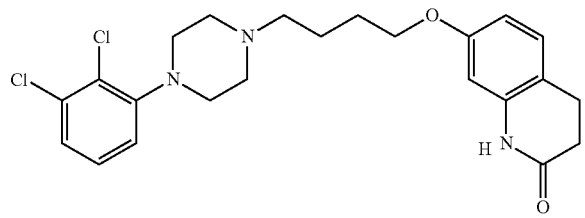

Aripiprazole is poorly soluble in water (<1 μg/mL at room temperature).

A long-acting aripiprazole sterile injectable formulation has merit as a drug dosage form in that it increases compliance of patients and thereby lowers the relapse rate in the treatment of schizophrenia.

Examples of known long-acting drug products for the treatment of schizophrenia include haloperidol decanoate and fluphenazine decanoate, both of which have an ester compound of low water solubility dissolved in sesame oil. Microcapsules containing risperidone (WO95/13814) and olanzapine (WO99/12549) are also known.

CITATION LIST

Patent Literature

PTL 1: U.S. Pat. No. 5,006,528
PTL 2: WO2005/041937
PTL 3: WO1995/13814
PTL 4: WO1999/12549
PTL 5: WO2003/26659

Non-Patent Literature

NPL 1: Journal of Pharmaceutical Sciences, Vol. 92, No. 2, 319-332 (2003)

SUMMARY OF INVENTION

Technical Problem

The present inventors attempted to develop a prefilled syringe (a prefilled syringe for injection to be prepared immediately before use) containing a freeze-dried aripiprazole formulation and water for injection, which are mixed together immediately before use to reconstitute a ready-to-use suspension.

To produce such a prefilled syringe, a freeze-dried aripiprazole formulation must be filled into a syringe. For the sake of convenience of such filling, a freeze-dried aripiprazole powder formulation is preferably used. In particular, to efficiently weigh out the amount of pharmaceutical preparation to be filled, a powder is preferably used.

To fill a powder into a syringe, methods using bulk powder itself or a spray-dried powder are generally used. However, when these methods are used, aripiprazole or particles containing aripiprazole exhibit poor dispersibility, and forming a homogeneous suspension within a syringe was impossible. Accordingly, an attempt was made to fill into a syringe a powder obtained by crushing the cake-form freeze-dried aripiprazole formulation disclosed in WO2005/041937. However, the resulting freeze-dried aripiprazole powder formulation exhibited poor dispersibility upon reconstitution with water; therefore, forming a homogeneous suspension was not easy. This result was unexpected, because the cake-form freeze-dried aripiprazole formulation is easily reconstituted into a homogeneous suspension by adding water thereto. (The above result was found by the present inventors and was previously unknown. The detail will be described below as a comparative example.)

The term "dispersibility" as used herein refers to the level of dispersion of the powder formulation in water when the water is added to the filled powder formulation. Accordingly, the phrase "exhibit poor dispersibility" or "poor dispersion" as used herein refers to the property such that when water is added to the filled powder formulation, water poorly penetrates into the powder, and the powder formulation does not easily disperse in water. When dispersed in water, the powder formulation obtained by crushing the cake-form freeze-dried aripiprazole formulation had problems such as formation of clumping and a portion remaining in a powder state due to no penetration of water.

Therefore, there was a need to develop a freeze-dried aripiprazole powder formulation that exhibits good dispersibility and is easily dispersed into a homogenous suspension upon reconstitution with water.

Solution to Problem

The invention of this application, for example, includes the items listed below. Hereinafter, "w/w %" stands for "(weight/weight) %", and "w/v %" stands for "(weight/volume) %".

Item 1a. A freeze-dried aripiprazole formulation obtained by a process comprising the steps of spraying for freezing an aripiprazole suspension containing
(I) aripiprazole,
(II) a vehicle for the aripiprazole, and
(III) water for injection; and
drying.

More specifically, the freeze-dried formulation of Item 1a can be described as in Item 1b below.

Item 1b. A freeze-dried formulation obtained by a process comprising the steps of spray-freezing an aripiprazole suspension containing
(I) aripiprazole,
(II) a vehicle for the aripiprazole, and
(III) water for injection
to form spray-frozen particles; and drying the spray-frozen particles to obtain spray-freeze-dried particles.

Item 2. The freeze-dried formulation according to Item 1a or 1b, consisting essentially of particles (spray-freeze-dried particles) with a particle size of substantially 30 µm or more (preferably 50 µm or more, more preferably 70 µm or more, and even more preferably 75 µm or more).

Item 3. The freeze-dried formulation according to any one of Items 1a to 2, comprising aripiprazole in an amount of 50 w/w % or more (preferably 60 w/w % or more, and more preferably 70 w/w % or more).

Item 4. The freeze-dried formulation according to any one of Items 1a to 3, which has a bulk density of 0.05 to 0.5 g/mL (preferably 0.08 to 0.4 g/mL, and more preferably 0.1 to 0.3 g/mL).

Item 5. The freeze-dried formulation according to any one of items 1a to 4, wherein the aripiprazole has a mean particle size of about 1 to about 10 microns.

Item 6. The freeze-dried formulation according to Item 5, wherein the aripiprazole has a mean particle size of about 2.5 microns.

Item 7a. The freeze-dried formulation according to any one of Item 1a to 6, comprising at least one member selected from the group consisting of suspending agents, bulking agents, and buffers.

Item 7b. The freeze-dried formulation according to any one of Item 1a to 7a, wherein the aripiprazole suspension contains as the vehicle at least one member selected from the group consisting of suspending agents, bulking agents, and buffers.

Item 8a. The freeze-dried formulation according to any one of Items 1a to 7b, comprising
(II-a) one or more suspending agents,
(II-b) one or more bulking agents, and
(II-c) one or more buffers.

Item 8b. The freeze-dried formulation according to any one of Items 1a to 8a, wherein the aripiprazole suspension contains, as the vehicle,
(II-a) one or more suspending agents,
(II-b) one or more bulking agents, and
(II-c) one or more buffers.

Item 9a. The freeze-dried formulation according to any one of Items 1a to 8b, comprising
(II-a) carboxymethyl cellulose or a salt thereof,
(II-b) mannitol, and
(II-c) sodium phosphate.

Item 9b. The freeze-dried formulation according to any one of Items 1a to 9a, wherein the aripiprazole suspension contains, as the vehicle,
(II-a) carboxymethyl cellulose or a salt thereof,
(II-b) mannitol, and
(II-c) sodium phosphate.

Item 10a. The freeze-dried formulation according to any one of Items 1a to 9b, further comprising (IV) a pH adjusting agent.

Item 10b. The freeze-dried formulation according to any one of Items 1a to 10a, wherein the aripiprazole suspension further comprises (IV) a pH adjusting agent.

Item 11. The freeze-dried formulation according to Item 10a or 10b, wherein the pH adjusting agent is sodium hydroxide.

Item 12. The freeze-dried formulation according to any one of Items 1a to 11, comprising
(I) aripiprazole,
(II-a) carboxymethyl cellulose or a sodium salt thereof,
(II-b) mannitol,
(II-c) sodium phosphate (to adjust pH to about 7), and optionally
(IV) sodium hydroxide (to adjust pH to about 7).

Item 13. The freeze-dried formulation according to any one of Items 1a to 12, wherein the aripiprazole is in the form of a monohydrate.

Item 14a. A process for producing a freeze-dried aripiprazole formulation comprising the steps of
(e'-1) spray-freezing an aripiprazole suspension having a mean particle size within the range of about 1 to about 10 microns to obtain spray-frozen particles; and
(e'-2) drying the spray-frozen particles to obtain spray-freeze-dried particles.

Item 14b. A process for producing a freeze-dried aripiprazole formulation comprising the steps of
(d') reducing the mean particle size of aripiprazole in a primary suspension formed by mixing aripiprazole, a vehicle for the aripiprazole, and water to the range of about 1 to about 10 microns to form a final suspension;
(e'-1) spray-freezing the aripiprazole suspension having a mean particle size of about 1 to about 10 microns to obtain spray-frozen particles; and
(e'-2) drying the spray-frozen particles to obtain spray-freeze-dried particles.

Item 14c. A process for producing a freeze-dried aripiprazole formulation comprising the steps of
(c') mixing aripiprazole, a sterile vehicle for the aripiprazole, and water to form a primary suspension;
(d') reducing the mean particle size of aripiprazole in the primary suspension to the range of about 1 to about 10 microns to form a final suspension;
(e'-1) spray-freezing the aripiprazole suspension having a mean particle size within the range of about 1 to about 10 microns to obtain spray-frozen particles; and
(e'-2) drying the spray-frozen particles to obtain spray-freeze-dried particles.

The processes of producing a freeze-dried aripiprazole formulation according to Items 14a to 14c are preferable as methods for producing the freeze-dried formulation of any one of Items 1a to 13.

Item 15. The process for producing a freeze-dried aripiprazole formulation according to any one of Items 1a to 13 comprising the steps of
(a) preparing sterile bulk aripiprazole having a desired particle size distribution;
(b) preparing a sterile vehicle for the sterile bulk aripiprazole;
(c) mixing the aripiprazole and the vehicle to form a sterile primary suspension containing the aripiprazole;
(d) reducing the mean particle size of the aripiprazole in the sterile primary suspension to the range of about 1 to about 10 microns to form a sterile final suspension; and
(e) spraying for freezing the final suspension, and drying.

Item 16. The process according to any one of Items 14a to 15, wherein the reduction of the mean particle size of aripiprazole in the (sterile primary) suspension is carried out by wet milling.

Item 17. The process according to any one of Items 14a to 16, wherein the spraying in step (e) or (e'-1) is either spraying at a low temperature for freezing or spraying under reduced pressure for freezing.

Item 18. The process according to any one of Items 14a to 17, further comprising selecting particles (spray-freeze-dried particles) with a particle size of 30 µm or more (preferably 50 µm or more, more preferably 70 µm or more, and even more preferably 75 µm or more).

Item 19. The freeze-dried formulation according to any one of Items 1a to 13, which exhibits good dispersibility and forms a homogenous aripiprazole suspension upon reconstitution with water.

Item 20. The freeze-dried formulation according to any one of Item 1a to 13 and 19, comprising particles with a particle size of less than 75 μm in an amount of 15 w/w % or less.

Item 21. A homogeneous aripiprazole suspension reconstituted from the freeze-dried formulation of any one of Items 1a to 13, 19, and 20 by adding water thereto.

Item 22. An aripiprazole formulation, which comprises aripiprazole and a vehicle for the aripiprazole and which is in the form of a powder (preferably having a particle size of 1 mm or less), the particles of the powder being spherical and porous.

Item 23. The aripiprazole formulation according to Item 22 comprising freeze-dried particles (preferably spray-freeze-dried particles) having a particle size of substantially 30 μm or more (preferably 50 μm or more, more preferably 70 μm or more, and even more preferably 75 μm or more).

Item 24. The aripiprazole formulation according to Item 22 or 23, comprising the aripiprazole in an amount of 50 w/w % or more (preferably 60 w/w % or more, and even more preferably 70 w/w % or more).

Item 25. The aripiprazole formulation according to any one of Items 22 to 24, which has a bulk density of 0.05 to 0.5 g/mL, more preferably 0.08 to 0.4 g/mL, and even more preferably 0.1 to 0.3 g/mL.

Item 26. The aripiprazole formulation according to any one of Items 22 to 25, wherein the aripiprazole has a mean particle size of about 1 to about 10 microns.

Item 27. The aripiprazole formulation according to Item 26, wherein the aripiprazole has a mean particle size of about 2.5 microns.

Item 28. The aripiprazole formulation according to any one of Items 22 to 27, comprising particles with a particle size of 75 μm or less in an amount of 15 w/w % or less.

Item 29. The aripiprazole formulation according to any one of Items 22 to 28, which is a freeze-dried formulation.

Item 30. The aripiprazole formulation according to item 29, which is a spray-freeze-dried formulation.

DESCRIPTION OF EMBODIMENTS

Figure 1:
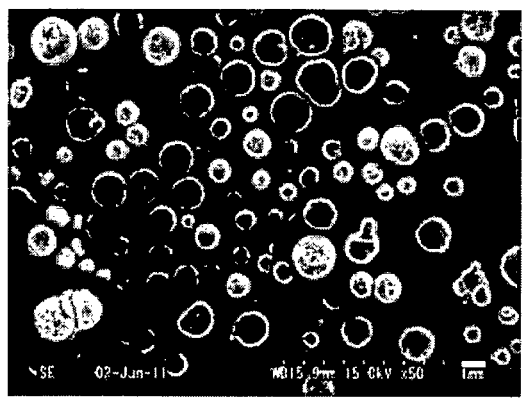
FIG. 1 shows the appearance (photo on the left) and surface condition (photo on the right) of spray-freeze-dried particles obtained by spray-freeze-drying a 10% suspension and collected between sieves of 75 μm and 250 μm. The white bar at the bottom right of the photo on the left indicates 1 mm, and the white bar at the bottom left of the photo on the right indicates 20 μm.
Figure 1:
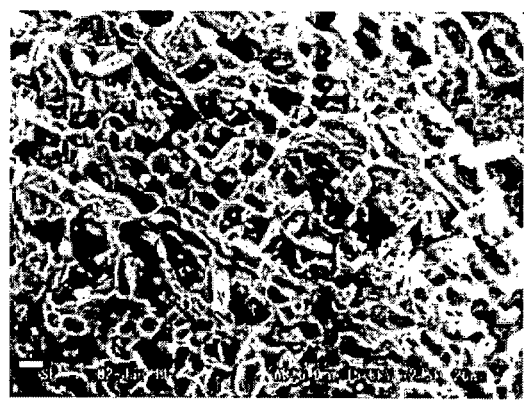

The present invention is described below in more detail. Naturally, "micron" indicates the same length as "μm."

The present invention provides the following pharmaceutical preparation:
a freeze-dried aripiprazole formulation obtained by a process comprising the steps of
spraying for freezing an aripiprazole suspension containing
(I) aripiprazole,
(II) a vehicle for the aripiprazole, and
(III) water for injection; and
drying.

This freeze-dried formulation is obtained by producing an aripiprazole suspension containing components (I) to (III) and then subjecting the suspension to spray-freeze-drying. The "aripiprazole suspension" is a homogeneous suspension. The "final aripiprazole suspension" obtained by the production process described below is particularly preferable.

This freeze-dried formulation is in the form of a powder, and exhibits good dispersibility in water. Accordingly, the freeze-dried formulation can be easily reconstituted into a homogenous suspension by adding water. The obtained suspension has the same properties as the suspension before being subjected to spray-freeze-drying. In particular, when the amount of water added for reconstitution is the same as the amount of water lost during freeze-drying, the obtained suspension has the same constitution and properties as the suspension before being subjected to spray-freeze-drying.

More specifically, the freeze-dried formulation upon reconstitution with water can form an injectable suspension that can release aripiprazole in a therapeutic amount over a period of at least 1 week, preferably 2, 3, or 4 weeks, and up to 6 weeks or more, when injected (preferably intramuscularly). The injectable suspension can release aripiprazole in a therapeutic amount for at least 1 week, preferably at least 2 weeks, more preferably at least 3 weeks, and even more preferably at least 4 weeks.

This freeze-dried formulation is in the form of a powder. This powder consists essentially of particles comprising (I) aripiprazole and (II) a vehicle for the aripiprazole. Because the freeze-dried formulation of the present invention is obtained by spray-freeze-drying the suspension, the obtained particles usually have a particle size of 1 mm or less. In the present specification, the particles are sometimes referred to as "spray-freeze-dried particles."

Although the reason is not clear, said spray-freeze-dried particles with an excessively small particle size unexpectedly tend to exhibit poor dispersibility, when water is added thereto for reconstitution. The powder formulation obtained by spray-freeze-drying usually does not contain particles with small particle sizes in such an amount as to cause poor dispersibility, and therefore removing the particles with small particle sizes is not particularly required but is preferable.

That is, the freeze-dried formulation preferably consists of particles with a particle size larger than a specific value. More specifically, the freeze-dried formulation preferably consists of particles with a particle size of substantially 30 μm or more, more preferably a particle size of substantially 50 μm or more, even more preferably a particle size of substantially 70 μm or more, and particularly preferably a particle size of 75 μm or more. Such a freeze-dried formulation can be obtained, for example, by sifting the spray-freeze-dried formulation using a sieve having a specific opening size. More specifically, for example, the freeze-dried formulation obtained by spray-freeze-drying the suspension is sifted using a sieve having an opening size of 30 μm, and the powder that remained on the sieve was collected to obtain a freeze-dried formulation with a particle size of "substantially 30 μm or more". The phrase "substantially 30 μm or more" means "obtained by a procedure for selecting particles of 30 μm or more (e.g., sifting) and does not mean containing no particles with a particle size of less than 30 μm.

Furthermore, even if it is not a "freeze-dried formulation consisting of particles with particle sizes larger than a specific value", any freeze-dried formulation that does not contain particles with small particle sizes in such an amount as to cause poor dispersibility can be preferably used. As described above, because the powder formulation obtained by spray-freeze-drying usually does not contain particles with small particle sizes in such an amount as to cause poor dispersibility, such a spray-freeze-dried formulation is preferable. Specific examples of such formulations include a freeze-dried formulation comprising particles with a particle size of less than 75 μm in an amount of preferably 15 w/w % or less, more preferably 10 w/w % or less, and even more preferably 8 w/w % or less. The proportion of the particles in the formulation can be determined by sifting using a sieve having an opening size of 75 μm, collecting a portion of the powder passing through the sieve, measuring the weight of the portion collected, and calculating the proportion of the portion, based on the total weight of the freeze-dried formulation.

The particle size of spray-freeze-dried particles depends on the fineness of the mist (size of mist droplets) during spraying, and thus can be suitably adjusted by adjusting the pressure for spraying, orifice of the spray nozzle, etc. at the time of spraying. Further, because the particles are produced by spray-freeze-drying, the particles can be approximately spherical.

The freeze-dried formulation (the spray-freeze-dried particles) of the present invention preferably contains aripiprazole in an amount of 50 w/w % or more, more preferably 60 w/w % or more, and even more preferably 70 w/w % or more.

The bulk density of the freeze-dried formulation of the present invention (i.e., spray-freeze-dried particles) is preferably 0.05 to 0.5 g/mL, more preferably 0.08 to 0.4 g/mL, and even more preferably 0.1 to 0.3 g/mL. The bulk density herein refers to a value obtained by pouring the freeze-dried formulation (powder) into a graduated cylinder and measuring the volume and weight of the formulation, and dividing the weight by the volume.

The vehicle may include one or more suspending agents, one or more bulking agents, and one or more buffers. More specifically, the vehicle is at least one member selected from the group consisting of suspending agents, bulking agents, and buffers.

The suspending agent is present in an amount of about 0.2 to about 10 w/v %, and preferably about 0.5 to about 5 w/v %, based on the sterile injectable formulation. The "sterile injectable formulation" as used herein refers to a sterile homogeneous aripiprazole suspension containing the above components (I) to (III) (including the suspension before spray-freeze-drying and the suspension obtained by reconstituting the freeze-dried formulation with water). Examples of suspending agents suitable for use include, but are not limited to, one, two, or more of the following: sodium carboxymethyl cellulose, hydroxypropyl cellulose, carboxymethyl cellulose, hydroxypropylethyl cellulose, hydroxypropylmethyl cellulose, and polyvinylpyrrolidone. Among these, sodium carboxymethyl cellulose and polyvinylpyrrolidone are preferable.

Other suspending agents suitable for use in the vehicle for the aripiprazole include various polymers, low-molecular-weight oligomers, natural products, and surfactants (including nonionic and ionic surfactants), such as cetyl pyridinium chloride, gelatin, casein, lecithin (phosphatide), dextran, glycerol, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., the commercially available Tweens (trademark), such as Tween 20 (trademark) and Tween 80 (trademark) (ICI Specialty Chemicals); polyethylene glycols (e.g., Carbowaxs 3350 (trademark) and 1450 (trademark); and Carbopol 934 (Union Carbide)), dodecyl trimethyl ammonium bromide, polyoxyethylene stearates, colloidal silicon dioxide, phosphates, sodium dodecylsulfate, carboxymethylcellulose ti calcium, hydroxypropyl celluloses (e.g., HPC, HPC-SL, and HPC-L), methylcellulose, hydroxyethylcellulose, hydroxypropylcellulose, hydroxypropyl methylcellulose phthalate, noncrystalline cellulose, magnesium aluminum silicate, triethanolamine, polyvinyl alcohol (PVA), 4-(1,1,3,3-tetramethylbutyl)-phenol polymer with ethylene oxide and formaldehyde (also known as tyloxapol, superione, and triton), poloxamers (e.g., Pluronics F68 (trademark) and F108 (trademark), which are block copolymers of ethylene oxide and propylene oxide); poloxamines (e.g., Tetronic 908 (trademark), also known as Poloxamine 908 (trademark), which is a tetrafunctional block copolymer derived from sequential addition of propylene oxide and ethylene oxide to ethylenediamine (BASF Wyandotte Corporation, Parsippany, N.J.)); charged phospholipids such as dimyristoyl phophatidyl glycerol, dioctylsulfosuccinate (DOSS); Tetronic 1508 (trademark) (T-1508) (BASF Wyandotte Corporation), dialkylesters of sodium sulfosuccinic acid (e.g., Aerosol OT (trademark), which is a dioctyl ester of sodium sulfosuccinic acid (American Cyanamid)); Duponol P (trademark), which is a sodium lauryl sulfate (DuPont); Tritons X-200 (trademark), which is an alkyl aryl polyether sulfonate (Rohm and Haas); Crodestas F-110, which is a mixture of sucrose stearate and sucrose distearate (Croda Inc.); p-isononylphenoxypoly-(glycidol), also known as Olin-10G (trademark) or Surfactant 10-G (trademark) (Olin Chemicals, Stamford, Conn.); Crodestas SL-400 (Croda, Inc.); and SA90HCO, which is $C_{18}H_{37}CH_2$ $(CON(CH_3))$—$CH_2(CHOH)_4(CH_2OH)_2$ (Eastman Kodak Co.); decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl-β-D-thioglucoside; n-hexyl β-D-glucopyranoside; nonanoyl-N-methylglucamide; n-nonyl β-D-glucopyranoside; octanoyl-N-methylglucamide; glucopyranoside; octyl β-D-thioglucopyranoside; and the like.

Most of these suspending agents are known pharmaceutical excipients and are described in detail in the Handbook of Pharmaceutical Excipients, published jointly by the American Pharmaceutical Association and The Pharmaceutical Society of Great Britain (The Pharmaceutical Press, 1986), specifically incorporated by reference. The suspending agents are commercially available and/or can be prepared by techniques known in the art. The suspending agents may be used singly or in a combination of two or more.

When the mean particle size of aripiprazole in the suspension is about 1 micron or more, carboxymethyl cellulose or sodium salts thereof are particularly preferable.

The bulking agent (also called "cryogenic/lyoprotectant") can be used in such an amount as to make the sterile injectable formulation approximately isotonic with blood at the time of administration. More specifically, bulking agent is present in an amount of about 1 to about 10 w/v %, preferably about 3 to about 8 w/v %, and more preferably about 4 to about 5 w/v %, based on the sterile injectable formulation. The "sterile injectable formulation" as used herein refers to a sterile homogeneous aripiprazole suspension containing the above components (I) to (III) (including the suspension before spray-freeze-drying and the suspension obtained by reconstituting the freeze-dried formulation with water). Examples of bulking agents suitable for use herein include, but are not limited to, one, two, or more of the following: mannitol, sucrose, maltose, xylitol, glucose, starches, sorbital, and the like. When the mean particle size of aripiprazole in the suspension is about 1 micron or more, mannitol is preferably used.

The buffer is used in an amount to adjust the pH of the aqueous suspension of the freeze-dried aripiprazole formulation to about 6 to about 8, and preferably about 7. To achieve such a pH, the buffer, depending on type, is usually used in an amount of about 0.02 to about 2 w/v %, preferably about 0.03 to about 1 w/v %, and more preferably about 0.1 w/v %, based on the total weight of the sterile injectable formulation. The "sterile injectable formulation" as used herein refers to a sterile homogeneous aripiprazole suspension containing the above components (I) to (III) (including the suspension before spray-freeze-drying and the suspension obtained by reconstituting the freeze-dried formulation with water). Examples of buffers suitable for use herein include, but are not limited to, one, two, or more of the following: sodium phosphate, potassium phosphate, and TRIS buffer. Among these, sodium phosphate is preferable.

The freeze-dried formulation of the invention may optionally contain a pH adjusting agent, which is used in an amount to adjust the pH of the suspension before spray-freeze-drying and the aqueous suspension of the freeze-dried aripiprazole (suspension obtained by reconstituting the freeze-dried formulation with water) to the range of about 6 to about 7.5, and preferably about 7, and may be an acid or base depending upon whether the pH of the aqueous suspension of the freeze-dried aripiprazole needs to be raised or lowered to reach the desired neutral pH of about 7. Thus, when the pH needs to be lowered, an acidic pH adjusting agent, such as hydrochloric acid or acetic acid, preferably hydrochloric acid, may be used. When the pH needs to be raised, a basic pH adjusting agent, such as sodium hydroxide, potassium hydroxide, calcium carbonate, magnesium oxide, or magnesium hydroxide, preferably sodium hydroxide, is used. Such pH adjusting agents can be used singly or in a combination of two or more.

The freeze-dried formulation of the present invention is obtained by spray-freezing the aripiprazole suspension containing the above components (I) to (III) to obtain spray-frozen aripiprazole particles, and drying the spray-frozen particles.

The spray-frozen particles contain components (I) to (III) (however, water for injection (III) is in the form of ice). When the spray-frozen particles are further subjected to drying, the water for injection (III) is removed from the particles to obtain particles containing components (I) and (II) (spray-freeze-dried particles). The spray-freeze-dried particles are porous (and may also be described as being in the form of foams. This is presumably because when the particles are dried, only the component (III)-derived ice portions in the spray-frozen particles are lost.

The spray-freeze-dried formulation is in the form of particles comprising components (I) and (II) as described above. The ratio of component (II) to component (I) in the particles is the same as that in the freeze-dried suspension.

More specifically, the amount of the suspending agent is preferably about 1 to about 5 parts by weight per 100 parts by weight of aripiprazole, the amount of the bulking agent is preferably about 5 to about 25 parts by weight per 100 parts by weight of aripiprazole, and the amount of the buffer is preferably about 0.05 to about 0.5 parts by weight per 100 parts by weight of aripiprazole.

Porosity may presumably be one of the reasons why the spray-freeze-dried particles have excellent dispersibility in water. However, regardless of the particle size of spray-freeze-dried particles, there is little difference in pore size of the particles, etc., whereas spray-freeze-dried particles with an excessively small particle size tend to have poor dispersibility in water, as described above. Accordingly, it is difficult to explain the dispersibility in water only from the viewpoint of porosity of the particles.

The present invention further provides a process for producing a freeze-dried formulation comprising the following steps:
(a) preparing bulk aripiprazole having a desired particle size distribution;
(b) preparing a vehicle for the bulk aripiprazole;
(c) mixing the aripiprazole, the sterile vehicle, and water to form a primary suspension;
(d) reducing the mean particle size of aripiprazole in the primary suspension to the range of about 1 to about 10 microns to form a final suspension; and
(e) spraying for freezing the final suspension, and drying to form a freeze-dried formulation.

Step (e) is a step of spray-freeze-drying the aripiprazole suspension. More specifically, step (e) can be divided separated into the following steps:
(e'-1) spray-freezing a suspension of aripiprazole with a mean particle size of about 1 to about 10 microns (corresponding to the final suspension) to obtain spray-frozen particles; and
(e'-2) drying the spray-frozen particles to obtain spray-freeze-dried particles.

As described above, in the production process, after the "primary aripiprazole suspension" is produced (step (c)), the mean particle size of aripiprazole in the primary suspension is reduced to obtain a "final aripiprazole suspension" (step (d)), and the final suspension is spray-frozen and dried (step (e)) to obtain a freeze-dried formulation.

The primary aripiprazole suspension as used herein simply means a suspension obtained by mixing bulk aripiprazole with the vehicle and water. The final aripiprazole suspension refers to a suspension obtained by milling aripiprazole to adjust the mean particle size of aripiprazole particles. The aripiprazole in the final suspension has a mean particle size of about 1 to about 10 μm. The final suspension is a homogeneous suspension. The homogeneous suspension as used herein refers to a "deflocculated suspension", which is a term used in the field of suspensions; it does not refer to a "flocculated suspension".

In the above method, reduction of the mean particle size of the primary suspension to a desired mean particle size is carried out by using an aseptic wet milling procedure, which preferably is aseptic wet ball milling. Aseptic wet milling is particularly preferable to form a homogeneous, sterile aripiprazole formulation of a desired mean particle size distribution.

The term "mean particle size" refers to volume mean diameter as measured by laser-light scattering (LLS) methods. The particle size distribution is measured by LLS methods, and the mean particle size is calculated from the particle size distribution. The LLS method is synonymous with the laser diffraction-scattering method.

The present invention further encompasses a process for producing a freeze-dried formulation comprising step (e), and a process for producing a freeze-dried formulation comprising steps (d) and (e), and a process for producing a freeze-dried formulation comprising steps (c) to (e).

The "process for producing a freeze-dried formulation comprising step (e)" can be paraphrased as follows:
a process for producing a freeze-dried aripiprazole formulation comprising the steps of
(e'-1) spray-freezing a suspension of aripiprazole with a mean particle size of about 1 to about 10 microns to obtain spray-frozen particles; and
(e'-2) drying the spray-frozen particles to obtain spray-freeze-dried particles.

The "process for producing the freeze-dried formulation comprising steps (d) and (e)" can be paraphrased as follows:
a process for producing a freeze-dried aripiprazole formulation comprising
the step (d') of reducing the mean particle size of aripiprazole in a primary suspension obtained by mixing aripiprazole, a sterile vehicle for the aripiprazole, and water to the range of about 1 to about 10 microns to obtain a final suspension; and the above steps (e'-1) and (e'-2).

The "process for producing a freeze-dried formulation comprising steps (c) to (e)" can be paraphrased as follows:
a process for producing a freeze-dried aripiprazole formulation comprising
the step (c') of mixing aripiprazole, a sterile vehicle for the aripiprazole, and water; and
the above steps (d'), (e'-1), and (e'-2).

The freeze-dried aripiprazole formulation of the present invention preferably contains aripiprazole in an amount of about 1 to about 40 w/w %, more preferably about 5 to about 35 w/w %, and even more preferably about 8 to about 30 w/w %, based on the weight of the suspension formulation obtained by reconstitution with water. That is, the amount of water used for reconstitution is preferably adjusted to achieve an aripiprazole content within the above mentioned range.

The aripiprazole preferably has a mean particle size of about 1 to about 30 microns, more preferably about 1 to about 20 microns, and even more preferably about 1 to about 10 microns. As described above, the "mean particle size" refers to volume mean diameter as measured by laser diffraction-scattering methods. The homogenous aripiprazole suspension containing components (I) to (III) (including the suspension before spray-freeze-drying and the suspension obtained by reconstituting the freeze-dried formulation with water) is measured by a laser diffraction-scattering method to determine the mean particle size of aripiprazole in the suspension.

When the desired controlled release period is at least about 2 weeks, and preferably about 3 to about 4 weeks, the mean particle size of the aripiprazole is within the range of about 1 to about 20 microns, preferably about 1 to about 10 microns, more preferably about 2 to about 4 microns, and most preferably about 2.5 microns. That is, when an injectable formulation is reconstituted from the freeze-dried formulation of the present invention having a mean particle size of aripiprazole within the specific range by adding water thereto, and administered, the period of controlled release of aripiprazole is at least 2 weeks, and may last for 6 weeks or more. The controlled release period is preferably 2 to 4 weeks, and more preferably 3 to 4 weeks. The aripiprazole contained in the freeze-dried formulation of the present invention that exhibits the above-mentioned controlled release period has a mean particle size of about 1 to about 20 microns, preferably about 1 to about 10 microns, and more preferably about 2 to about 4 microns, and even more preferably about 2.5 microns.

The aripiprazole having a mean particle size of about 2.5 microns has, for example, a particle size distribution as follows:

TABLE 1

| Preferred | More Preferred |
| --- | --- |
| 95% <50 microns | 95% <30 microns |
| 90% <20 microns | 90% <15 microns |
| 50% <10 microns | 75% <10 microns |
| 10% <2 microns | 50% <4 microns |
| | 10% <1 micron |

The method for producing the freeze-dried aripiprazole formulation of the invention is preferably carried out with everything being sterile. Accordingly, an aseptic procedure is used to produce sterile bulk aripiprazole of a desired particle size distribution. The sterile bulk aripiprazole has a mean particle size of about 5 to about 1000 microns, and preferably about 110 to about 500 microns.

The impinging jet crystallization method and the aseptic crystallization method are preferably used to produce bulk sterile aripiprazole.

The vehicle for sterile bulk aripiprazole, which contains a suspending agent, a bulking agent, a buffer, and water and may optionally contain a pH adjusting agent, is prepared and sterilized. The sterile bulk aripiprazole and the sterile vehicle are then aseptically mixed to form a sterile primary suspension. The particle size of the aripiprazole is reduced to a desired level by wet milling. This is preferably carried out by an aseptic wet milling procedure wherein sterile particles of aripiprazole dispersed in the sterile vehicle are subjected to grinding means in the presence of grinding media to reduce the particle size of aripiprazole to the range of preferably about 1 to about 20 microns, more preferably about 1 to about 10 microns, even more preferably about 2 to 4 microns, and particularly preferably about 2.5 microns, depending on the desired controlled release period.

The aseptic wet milling procedure is preferably a high-pressure homogenizer method or wet ball milling. A high-pressure homogenizer method is more preferable. The desired mean particle size of aripiprazole is preferably achieved by reducing the mean particle size in a high-shear pre-milling step prior to wet milling using a high-pressure homogenizer, and then reducing the mean particle size by a high-pressure homogenizer to a desired particle size.

In addition to ball mills (such as Dyno mills) and the high-pressure homogenizer method, other low-energy and high-energy mills (such as a roller mill) may be used, and high-energy mills (such as Netzsch mills, DC mills, and Planetary mills) may be used. However, the milling procedure and equipment used are required to be able to produce a sterile aripiprazole formulation of a desired mean particle size.

Other techniques for particle size reduction that may be used include aseptic controlled crystallization, high shear homogenization, and microfluidization to produce particles having a mean particle size in the range of about 1 to about 100 microns (preferably about 1 to about 20 microns, more preferably about 1 to about 10 microns, even more preferably about 2 to about 4 microns, and particularly preferably about 2.5 microns).

The spray-freezing step of the present invention (i.e., spraying for freezing) may be performed according to known methods. Examples of usable methods include, but are not limited to, a method of spraying into liquid nitrogen, a method of spraying at low temperatures for freezing, and a method of spraying under reduced pressure for freezing due to heat of vaporization of the liquid.

The step of drying the spray-frozen particles obtained by the spray-freezing step can also be performed according to known methods. However, drying is preferably performed while the particles are maintained in a frozen state. Accordingly, the drying step is preferably performed at low temperatures (the temperature at which ice sublimes: for example, at about −5° C. or less). Furthermore, lowering the pressure in the dryer can promote drying and is thus preferable. For example, adjusting the air pressure to 50 Pa or less, preferably 20 Pa or less, is preferable. More specifically, for example, the spray-frozen particles are placed in a freeze dryer and maintained at −5° C. at 20 Pa or less for at least 24 hours to achieve drying. Before the drying, a step of maintenance in a frozen state may be performed. For example, before drying, spray-frozen particles may be maintained at a low temperature (e.g., about −40° C.) for about 1 to about 5 hours, and then dried. By maintaining the frozen state, even the inside of the frozen particles can be firmly frozen. (The spray-freeze-dried particles, including the inside thereof, are flash-frozen when spray-dried, but just to be safe, a step of maintaining the frozen state may be included.)

Aripiprazole may be used in a desired crystalline form. Examples thereof include a monohydrate form (aripiprazole hydrate A) and a number of anhydrous forms, namely, Anhydride Crystals B, Anhydride Crystals C, Anhydride Crystals D, Anhydride Crystals E, Anhydride Crystals F, and Anhydride Crystals G. The above crystal forms and other crystal forms of aripiprazole and methods for making such crystal forms are disclosed in WO 2003/26659, published on Apr. 4, 2003.

As described above, the aripiprazole is present in an amount of about 1 to about 40 w/v %, preferably about 5 to about 35 w/v %, and more preferably about 8 to about 30 w/v %, in the aqueous injectable formulation, i.e., suspension. In preferred embodiments, the freeze-dried aripiprazole formulation is constituted with water for injection in an amount to provide about 10 to about 800 mg, preferably about 200 to about 600 mg of aripiprazole in a volume of 2.5 mL or less, preferably 2 mL of the formulation. More specifically, the aripiprazole is preferably present in the aqueous injectable formulation, i.e. suspension, in an amount of about 50 to about 800 mg/2 mL of the formulation, more preferably about 100 to about 700 mg/2 mL of the formulation, even more preferably about 160 to about 600 mg/2 mL of the formulation, and still even more preferably about 200 to about 600 mg/2 mL of the formulation. Such a suspension is administered once every 2 to 6 weeks (i.e., once every 2, 3, 4, 5 or 6 weeks), as described above. The suspension as used herein includes the suspension before spray-freeze-drying and the suspension obtained by reconstituting the freeze-dried formulation with water. However, as described above, the concentration of the reconstituted suspension varies depending on the amount of water used for reconstitution. Accordingly, the suspension before spray-freeze-drying, and the suspension obtained by reconstituting the freeze-dried formulation with water do not necessarily have the same concentration, and may have different concentrations.

In the above process for producing the freeze-dried formulation, the mean particle size of aripiprazole in the aripiprazole suspension is described. Because the freeze-dried formulation of the present invention is obtained by spray-freeze-drying the aripiprazole suspension as described above, the mean particle size of aripiprazole contained in the freeze-dried formulation is the same as that of aripiprazole contained in the suspension used for the production of the formulation.

Accordingly, the mean particle size of aripiprazole contained in the freeze-dried formulation (spray-freeze-dried particles) of the present invention is preferably about 1 to about 20 microns, more preferably about 1 to about 10 microns, even more preferably about 2 to about 4 microns, and particularly preferably about 2.5 microns.

In the suspension obtained by reconstituting the freeze-dried formulation of the present invention with water, the vehicle is dissolved in water. Therefore, the mean particle size of aripiprazole contained in the freeze-dried formulation can be easily obtained by measuring the mean particle size of aripiprazole in the suspension by a laser diffraction-scattering method. The mean particle size of aripiprazole contained in the freeze-dried formulation of the present invention is measured in this manner.

Preferable examples of reconstituted suspension formulations obtained by the present invention are as follows:

TABLE 2

| Aripiprazole | 100 mg | 200 mg | 400 mg |
| Carboxymethyl cellulose | 9 mg | 9 mg | 9 mg |
| Mannitol | 45 mg | 45 mg | 45 mg |
| Sodium phosphate | 0.8 mg | 0.8 mg | 0.8 mg |
| Sodium hydroxide | q.s. to adjust pH to 7 | q.s. to adjust pH to 7 | q.s. to adjust pH to 7 |
| Water for injection | q.s. to 1 ml | q.s. to 1 ml | q.s. to 1 ml |

After reconstitution of the suspension formulation with water, the aripiprazole formulation of the invention is used to treat schizophrenia and related disorders (such as bipolar disorder and dementia) in human patients. A preferable dosage for the injectable formulation of the invention is about 100 to about 400 mg of aripiprazole per dose. This amount of aripiprazole is administered by a single injection or multiple injections. The formulation can be administered once or twice monthly. More specifically, a preferable dosage is a single injection or multiple injections containing about 100 to about 400 mg aripiprazole/mL given once or twice monthly. The injectable formulation is preferably administered intramuscularly, although subcutaneous injection is acceptable as well.

The following Examples represent preferred embodiments of the invention. The unit "%" for the concentration of the suspension means "w/v %".

EXAMPLES

Preparation of 10%, 20%, and 30% aripiprazole suspensions

First, a 30% suspension was prepared. More specifically, each component was dissolved or suspended in water to prepare a suspension (primary suspension) finally containing 12.48 mg of carboxymethyl cellulose, 62.4 mg of mannitol, and 1.11 mg of sodium dihydrogen phosphate monohydrate, and 312.0 mg of aripiprazole hydrate per mL of the suspension. The pH of the primary suspension was adjusted to about 7 with sodium hydroxide. The primary suspension was pre-milled with a shear rotary homogenizer (Clearmix, a product of M Technique Co., Ltd.), and then repeatedly subjected to wet milling at about 550 bar using a high-pressure homogenizer (a product of Niro) to achieve a mean particle size of aripiprazole of 3 µm or less, thus providing a suspension (final suspension) of about 30% aripiprazole. The 30% aripiprazole suspension was diluted with water to prepare a 10% Suspension and a 20% suspension.

Spray-Freeze-Drying of the Suspensions

About 100 mL of each suspension of these different concentrations was placed into each spraying bottle (product number: 4-5002-01, a product of AS ONE Corporation, type that sprays by squeezing a trigger by hand). Liquid nitrogen was placed on an aluminum tray of about 250 mm×about 300 mm to a depth of about 10 mm. Each suspension was sprayed over the liquid nitrogen surface from a height of about 200 mm until each spraying bottle was empty. As a result, each of the suspensions sprayed into liquid nitrogen was frozen in the form of grains to form spray-frozen particles. After spraying and before liquid nitrogen had volatilized off from the aluminum tray, the tray over which each suspension of the different concentrations was sprayed was transferred to a shelf of a freeze dryer pre-cooled to −40° C. to start freeze-drying. The freeze-drying conditions were as follows:

(a) Maintenance of the frozen state: the product was maintained at −40° C. for at least 3 hours.

(b) Drying: the chamber pressure was adjusted to about 20 Pa or less, the shelf temperature was raised to about 5° C., and drying was continued under these conditions for at least 24 hours.

In this Example, the freezing step was performed by spraying into liquid nitrogen. However, insofar as spray-freezing can be performed, the method is not limited thereto. For example, a method comprising spraying at a low temperature for freezing, and a method comprising spraying under reduced pressure for freezing due to heat of vaporization of the liquid can be used.

Sifting of the Obtained Freeze-Dried Products

After freeze-drying, each of the obtained freeze-dried products was placed on a sieve with a diameter of 80 mm and with a mesh size (i.e., an opening size) of 1000 μm. Sieves with mesh sizes of 500 μm, 250 μm, and 75 μm were stacked together below the sieve with a mesh size of 1000 μm, and sifting was performed. The freeze-dried products that remained between the sieves of 75 μm and 250 μm, those that remained between the sieves of 250 μm and 500 μm, and those that remained between the sieves of 500 μm and 1000 μm were collected. Hereinafter, the freeze-dried product (particles) that remained between sieves of specific mesh sizes and collected therefrom may also be described as "particles collected between sieves of a smaller mesh size and a larger mesh size". For example, the freeze-dried product that remained between the sieves of 75 μm and 250 μm and collected therefrom is described as "particles collected between sieves of 75 μm and 250 μm".

The sieves used herein are sieves of Japanese Pharmacopoeia 16th edition Sieve No. 200 (opening size: 75 μm), No. 60 (opening size: 250 μm), No. 30 (opening size: 500 μm), and No. 16 (opening size 1000 μm).

Evaluation 1 of the Obtained Freeze-Dried Products

Figure 2:
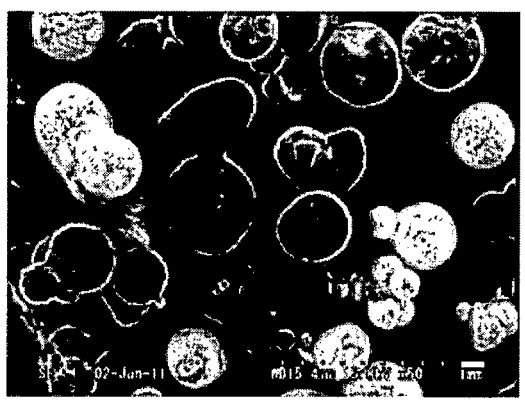
FIG. 2 shows the appearance (photo on the left) and surface condition (photo on the right) of spray-freeze-dried particles obtained by spray-freeze-drying a 10% suspension and collected between sieves of 250 μm and 500 μm. The white bar at the bottom right of the photo on the left indicates 1 mm, and the white bar at the bottom right of the photo on the right indicates 20 μm.
Figure 2:
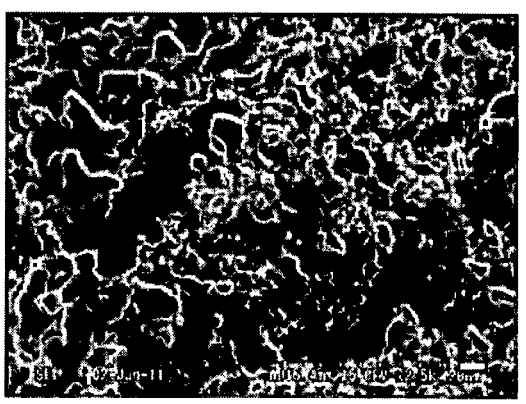
Figure 3:
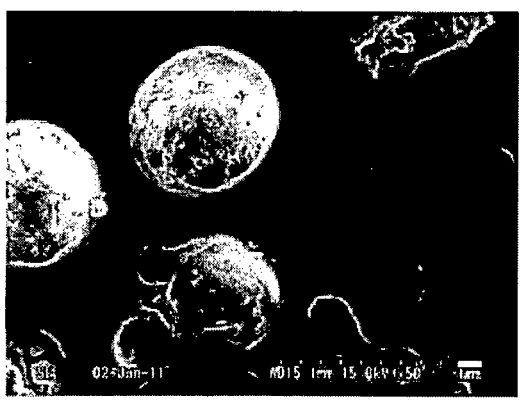
FIG. 3 shows the appearance (photo on the left) and surface condition (photo on the right) of spray-freeze-dried particles obtained by spray-freeze-drying a 10% suspension and collected between sieves of 500 μm and 1000 μm. The white bar at the bottom right of the photo on the left indicates 1 mm, and the white bar at the bottom right of the photo on the right indicates 20 μm.
Figure 3:
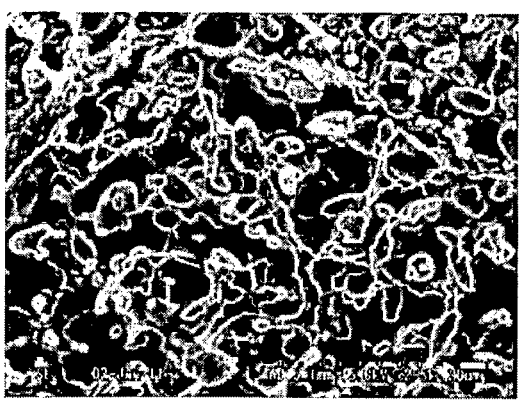
Figure 4:
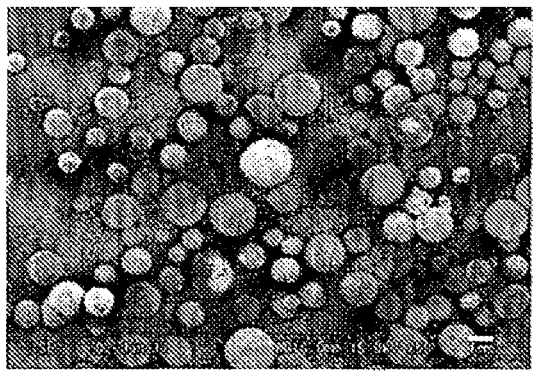
FIG. 4 shows the appearance (photo on the left) and surface condition (photo on the right) of spray-freeze-dried particles obtained by spray-freeze-drying a 20% suspension and collected between sieves of 75 μm and 250 μm. The white bar at the bottom right of the photo on the left indicates 1 mm, and the white bar at the bottom right of the photo on the right indicates 20 μm.
Figure 4:
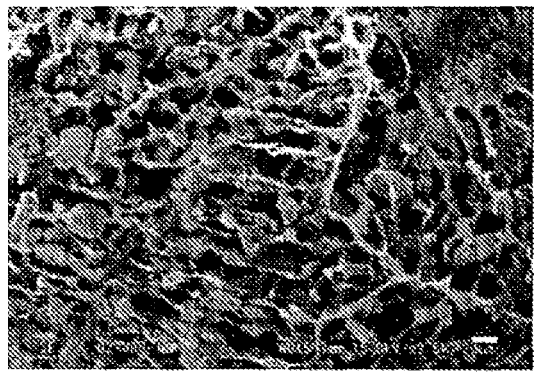
Figure 5:
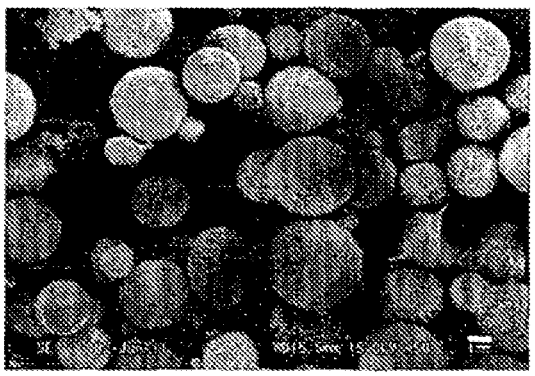
FIG. 5 shows the appearance (photo on the left) and surface condition (photo on the right) of spray-freeze-dried particles obtained by spray-freeze-drying a 20% suspension and collected between sieves of 250 μm and 500 μm. The white bar at the bottom right of the photo on the left indicates 1 mm, and the white bar at the bottom right of the photo on the right indicates 20 μm.
Figure 5:
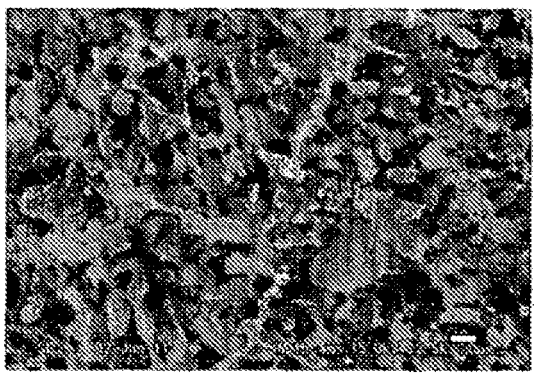
Figure 6:
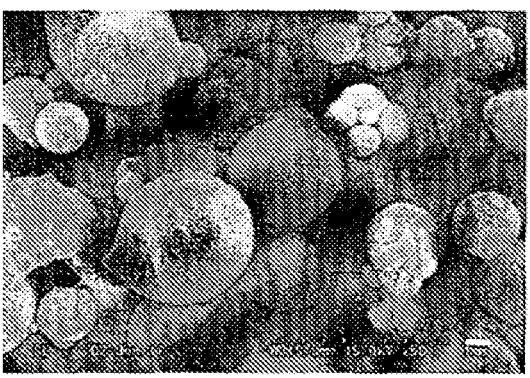
FIG. 6 shows the appearance (photo on the left) and surface condition (photo on the right) of spray-freeze-dried particles obtained by spray-freeze-drying a 20% suspension and collected between sieves of 500 μm and 1000 μm. The white bar at the bottom right of the photo on the left indicates 1 mm, and the white bar at the bottom right of the photo on the right indicates 20 μm.
Figure 6:
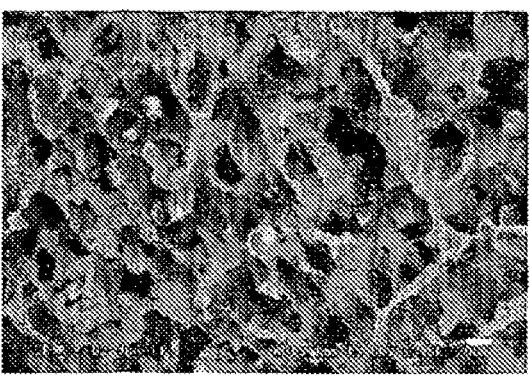
Figure 7:
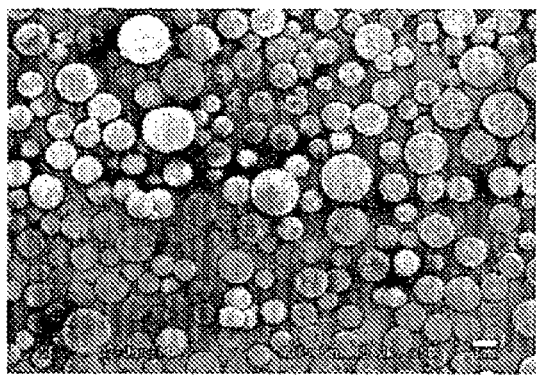
FIG. 7 shows the appearance (photo on the left) and surface condition (photo on the right) of spray-freeze-dried particles obtained by spray-freeze-drying a 30% suspension and collected between sieves of 75 μm and 250 μm. The white bar at the bottom right of the photo on the left indicates 1 mm, and the white bar at the bottom left of the photo on the right indicates 20 μm.
Figure 7:
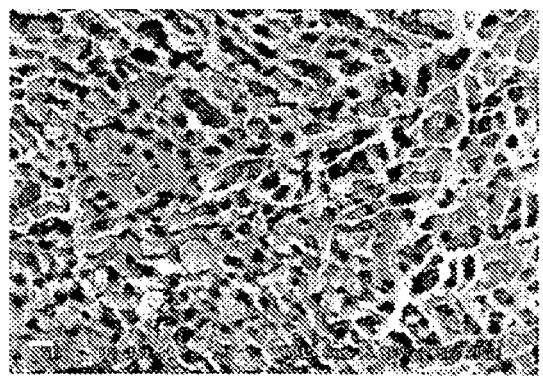
Figure 8:
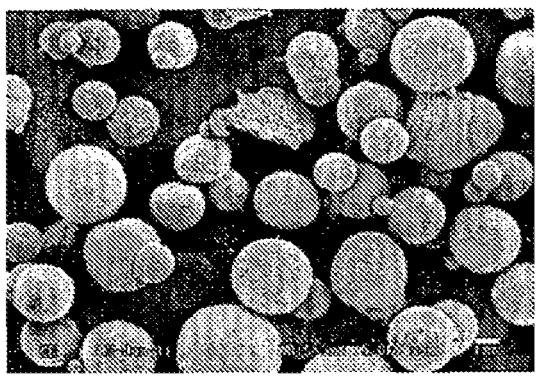
FIG. 8 shows the appearance (photo on the left) and surface condition (photo on the right) of spray-freeze-dried particles obtained by spray-freeze-drying a 30% suspension and collected between sieves of 250 μm and 500 μm. The white bar at the bottom right of the photo on the left indicates 1 mm, and the white bar at the bottom right of the photo on the right indicates 20 μm.
Figure 8:
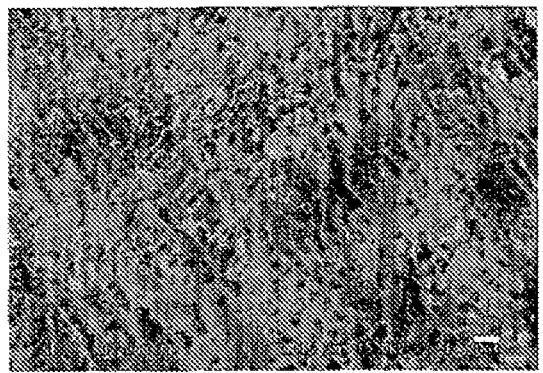
Figure 9:
FIG. 9 shows the appearance (photo on the left) and surface condition (photo on the right) of spray-freeze-dried particles obtained by spray-freeze-drying a 30% suspension and collected between sieves of 500 μm and 1000 μm. The white bar at the bottom right of the photo on the left indicates 1 mm, and the white bar at the bottom right of the photo on the right indicates 20 μm.
Figure 9:
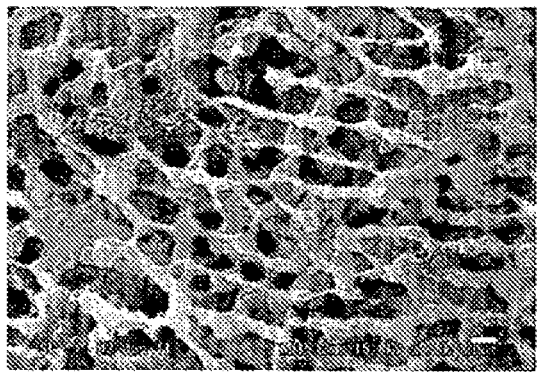

The obtained freeze-dried products were observed with a scanning electron microscope. FIGS. 1 to 9 show the results. FIGS. 1 to 3 show the results of freeze-dried products obtained using the 10% suspension. FIGS. 4 to 6 show the results of freeze-dried products obtained using the 20% suspension. FIGS. 7 to 9 show the results of freeze-dried products obtained using the 30% suspension. FIGS. 1, 4, and 7 show the appearance (photo on the left) and surface condition (photo on the right) of the particles collected between the sieves of 75 μm and 250 μm. FIGS. 2, 5, and 8 show the appearance (photo on the left) and surface condition (photo on the right) of the particles collected between the sieves of 250 μm and 500 μm. FIGS. 3, 6, and 9 show the appearance (photo on the left) and surface condition (photo on the right) of the particles collected between the sieves of 500 μm and 1000 μm. All of the freeze-dried products appeared to be approximately spherical and porous. FIGS. 1 to 9 illustrate 50× magnifications of the appearance (photo on the left) and 2500× magnifications of the surface condition (photo on the right).

The bulk density of the obtained freeze-dried products was measured. More specifically, the freeze-dried product (powder) was inserted into a 25-mL graduated cylinder up to the 5-mL mark, and the inserted powder weight was measured to calculate the bulk density. As a result, the bulk density was about 0.1 to about 0.3 g/mL.

About 325 mg of each powder (about 250 mg in terms of aripiprazole) was weighed out and placed into glass vials. Water for injection was added thereto in an amount to prepare an aripiprazole suspension of approximately 20%. Each vial was capped with a rubber stopper and shaken by hand to obtain a resuspension (i.e., a suspension reconstituted by adding water for injection). The powder was easily resuspended just like the vial-freeze-dried product (corresponding to the cake-form freeze-dried aripiprazole formulation disclosed in WO2005/041937) with no observation of powder agglomerates due to poor dispersion.

The resuspension in the vial was sucked from the vial using a needle-unattached plastic syringe having an orifice portion with an inner diameter of about 1.7 mm to which a needle is to be attached. No powder remaining due to poor dispersion was observed in the vial after sucking. A 27G needle (inner diameter: 0.22 mm) was attached to this syringe to eject the suspension. The suspension was ejected without needle clogging. The results confirmed that the obtained resuspension of the freeze-dried product contained no powder agglomerates with a size of 1.7 mm or more, and no aggregates that may cause clogging of a needle with an inner diameter of 0.22 mm were formed.

The mean particle size after resuspension was measured by a SALD-3100 laser diffraction particle size distribution analyzer, produced by Shimadzu Corporation. The measurement was performed using a circulation cell with a refractive index of 2.00-0.20i using water as a medium for measurement. More specifically, 330 mL of water was circulated through a sensing station within a measuring apparatus, and about 0.05 mL of the suspension to be measured was added thereto and measured. The suspension was ultrasonically treated for 1 minute using an ultrasonic generator accompanying the particle size distribution analyzer of the suspension. The mean particle size of the suspension after the ultrasonication was measured in the same manner as above. When a reduction in mean particle size of 0.5 μm or more was observed in the measurement with ultrasonic treatment, it was assessed as "aggregated". In the present invention, the term "mean particle size" refers to a volume mean diameter as measured by a laser-light scattering (LLS) method, i.e., a laser diffraction-scattering method. Particle size distribution was measured by this method, and mean particle size was calculated from the particle size distribution. Table 3 shows, the measurement results. The measurement results indicate that no aggregation was observed in any case and that all the freeze-dried products were resuspended with good redispersibility.

TABLE 3

| Suspension | Mesh sizes of the sieves used for collection | Bulk density (g/mL) | Mean particle size after re-dispersion (μm) | |
|---|---|---|---|---|
| | | | Measured without ultrasonic treatment | Measured with ultrasonic treatment |
| 10% | 75 μm and 250 μm | 0.131 | 1.92 | 1.98 |
| | 250 μm and 500 μm | 0.123 | Not measured | Not measured |
| | 500 μm and 1000 μm | 0.107 | Not measured | Not measured |
| 20% | 75 μm and 250 μm | 0.178 | 1.97 | 1.96 |
| | 250 μm and 500 μm | 0.170 | Not measured | Not measured |
| | 500 μm and 1000 μm | 0.147 | Not measured | Not measured |
| 30% | 75 μm and 250 μm | 0.266 | 1.98 | 1.98 |
| | 250 μm and 500 μm | 0.238 | Not measured | Not measured |
| | 500 μm and 1000 μm | 0.200 | 2.06 | 2.06 |

Evaluation 2 of the Obtained Freeze-Dried Products

A 10% aripiprazole suspension was spray-freeze-dried in the same manner as above to obtain a freeze-dried product. The freeze-dried product was transferred onto a sieve with a mesh size of 250 μm and a diameter of 80 mm. A sieve with a mesh size of 75 μm was placed below the sieve with a mesh size of the 250 μm, and a tray was provided under the sieve with a mesh size of 75 μm. The freeze-dried product was sifted thereby. The freeze-dried product that remained between the sieves of 75 μm and 250 μm, and the freeze-dried product that passed through the sieve of 75 μm and remained on the tray were collected.

As a comparative example, a freeze-dried product was prepared by freeze-drying a suspension in a vial (vial-freeze-dried product). More specifically, the freeze-dried product was produced in the following manner.

First, a 10% suspension was prepared in the following manner. More specifically, each component was dissolved or suspended in water to prepare a suspension (primary suspension) finally containing 4.16 mg of carboxymethyl cellulose, 20.8 mg of mannitol, and 0.37 mg of sodium dihydrogen phosphate monohydrate, and 104.0 mg of aripiprazole hydrate, per mL of the suspension. The pH of the primary suspension was adjusted to about 7 with sodium hydroxide. The primary suspension was pre-milled with a shear rotary homogenizer (Clearmix, a product of M Technique Co., Ltd.), and then repeatedly subjected to wet milling at about 550 bar using a high-pressure homogenizer (a product of Niro) to achieve a mean particle size of aripiprazole of 3 μm or less. A suspension (final suspension) of about 10% aripiprazole was thereby obtained. The final suspension was the same as the 10% suspension obtained in the above "preparation of the 10%, 20%, and 30% aripiprazole suspensions".

A 4.75 mL quantity of this suspension was placed in a glass vial with a diameter of 23 mm and a height of 43 mm and freeze-dried under the following conditions:
(a) Maintenance of the frozen state: the product was maintained at −40° C. for at least 3 hours.
(b) Drying: the chamber pressure was adjusted to about 20 Pa or less, the shelf temperature was raised to −5° C., and drying was continued under these conditions for at least 24 hours.

After freeze-drying, a vial-freeze-dried product was obtained. The vial-freeze-dried product corresponds to the cake-form freeze-dried aripiprazole formulation disclosed in WO2005/041937.

The vial-freeze-dried product was crushed into a powder in the vial with a spatula. The obtained powder was removed from the vial and transferred onto a sieve with a mesh size of 250 μm and a diameter of 80 mm. A sieve with a mesh size of 75 μm was placed below the sieve with a mesh size of the 250 μm, and a tray was provided under the sieve with a mesh size of 75 μm. The freeze-dried product was sifted thereby. The freeze-dried product that remained between the sieves of 75 μm and 250 μm, and the freeze-dried product that passed through the sieve of 75 μm and remained on the tray were collected.

<Microscopic Observation>

Figure 10:
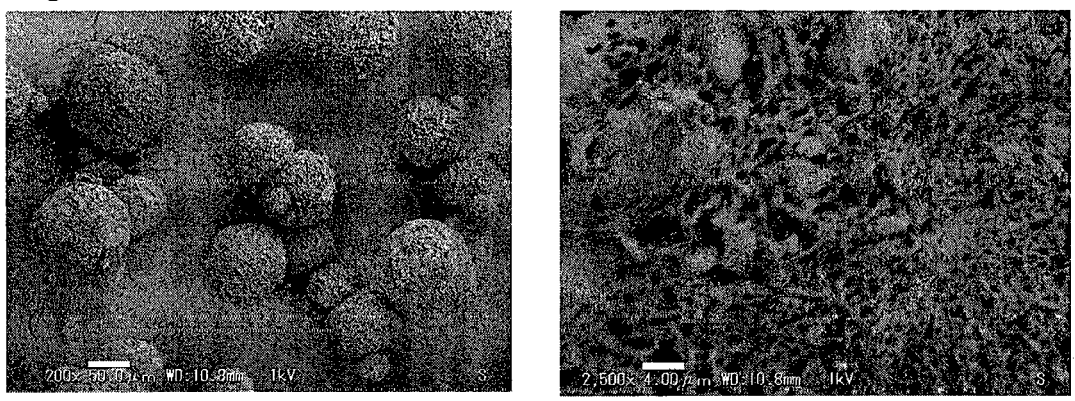
FIG. 10 shows the appearance (photo on the left) and surface condition (photo on the right) of spray-freeze-dried particles obtained by spray-freeze-drying a 10% suspension and collected between sieves of 75 μm and 250 μm. The white bar at the bottom right of the photo on the left indicates 50 μm, and the white bar at the bottom left of the photo on the right indicates 4 μm.
Figure 11:
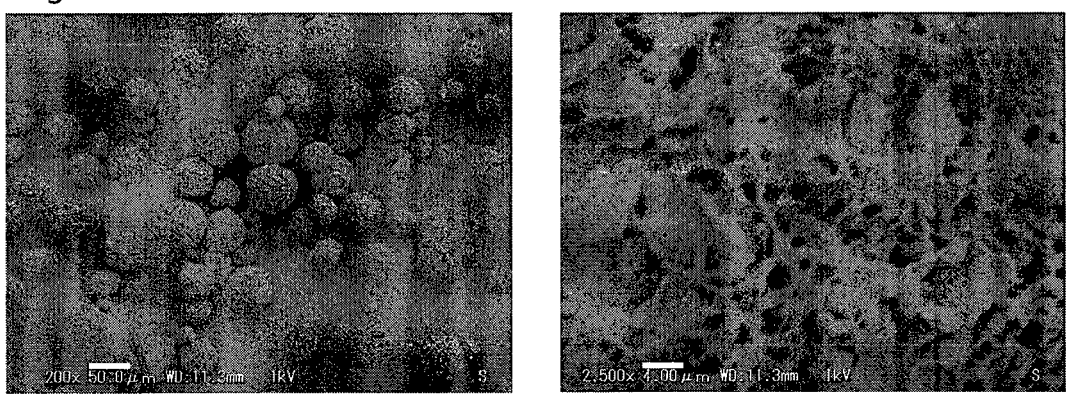
FIG. 11 shows the appearance (photo on the left) and surface condition (photo on the right) of spray-freeze-dried particles that were obtained by spray-freeze-drying a 10% suspension and that passed through a sieve of 75 μm. The white bar at the bottom right of the photo on the left indicates 50 μm, and the white bar at the bottom left of the photo on the right indicates 4 μm.
Figure 12:
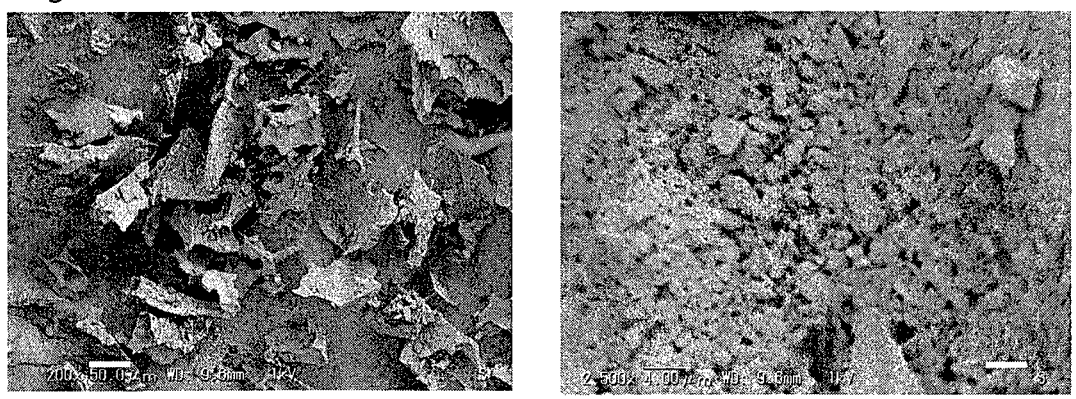
FIG. 12 shows the appearance (photo on the left) and surface condition (photo on the right) of the powder obtained by crushing a product freeze-dried in a vial ("vial-freeze-dried product") and collected between sieves of 75 μm and 250 μm. The white bar at the bottom right of the photo on the left indicates 50 μm, and the white bar at the bottom left of the photo on the right indicates 4 μm.
Figure 13:
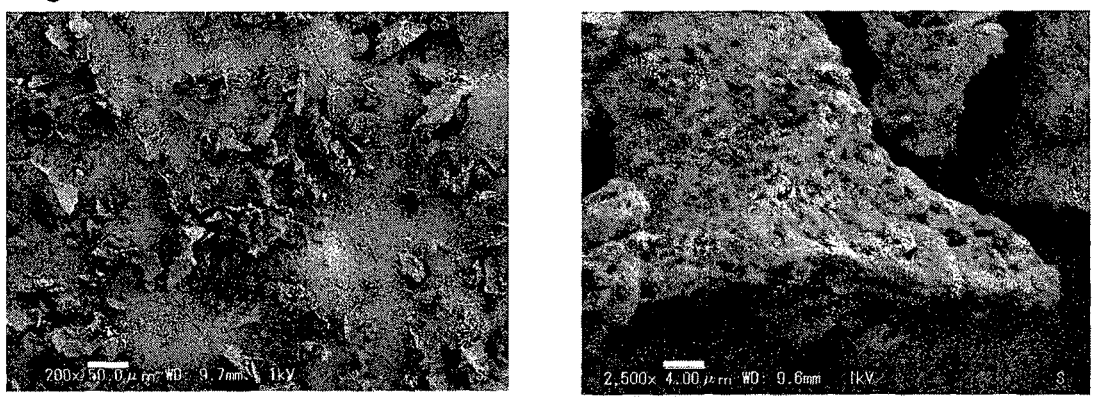
FIG. 13 shows the appearance (photo on the left) and surface condition (photo on the right) of the powder that was obtained by crushing a vial-freeze-dried product and that passed through a sieve of 75 μm. The white bar at the bottom right of the photo on the left indicates 50 μm, and the white bar at the bottom left of the photo on the right indicates 4 μm.

Each of the freeze-dried products collected was observed with a scanning electron microscope. FIGS. 10 to 13 show the results. FIGS. 10 and 11 show the results of the spray-freeze-dried product. FIGS. 12 and 13 show the results of the powder obtained from the vial-freeze-dried product. FIGS. 10 and 12 show the appearance (photo on the left) and surface condition (photo on the right) of the particles collected between the sieves of 75 μm and 250 μm. FIGS. 11 and 13 show the appearance (left) and surface condition (photo on the right) of the particles that passed though the sieve of 75 μm. FIGS. 10 to 13 illustrate 200× magnifications of the appearance (photo on the left) and 2500× magnifications of the surface condition (photo on the right).

The particles of the spray-freeze-dried product that passed through the sieve of 75 μm and those that remained on the sieve of 75 μm were both spherical and porous. There was no difference therebetween in the surface condition.

With respect to the particles of the powder obtained by crushing the vial-freeze-dried product, the particles that passed through the 75 μm sieve and those that remained on the sieve of 75 μm were both irregularly shaped. There was no difference therebetween in the surface condition.

<Evaluation of Dispersibility in Water>

The powders obtained by sifting were placed in vials with a diameter of 23 mm and a height of 43 mm in an amount such that each vial contained about 475 mg of aripiprazole. Each vial was capped with a rubber stopper. The freeze-dried product obtained by spray-freeze-drying contained only a very small amount of particles that passed through the sieve of 75 μm. Accordingly, sifting was repeated many times to collect the particles in an amount of about 475 mg in terms of aripiprazole.

On the assumption that vibration would occur due to transport, the bottom of each vial was lightly tapped 5 times. Thereafter, the rubber stopper was removed and 1.9 mL of water was added to the vial. After the vial was capped again with the rubber stopper, the vial was gently shaken by hand 5 times. After shaking, the rubber stopper was removed and the vial was inverted to remove the contents from the vial. Air was lightly blown onto the contents and the dispersibility in water was observed. The vial-freeze-dried product before being crushed with a spatula (i.e., cake-form freeze-dried product) was also investigated in the same manner as above. FIGS. 14 to 17 show the observation results.

Figure 14:
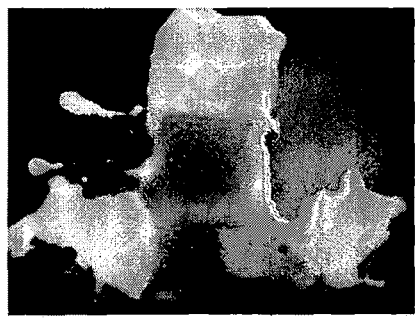
FIG. 14 shows the appearance of a suspension obtained by dispersing an uncrushed (cake-form) vial-freeze-dried product in water.

The (cake-form) vial-freeze-dried product was easily redispersed without problems, and no agglomerates were observed in the suspension removed from the vial (FIG. 14).

Figure 15:
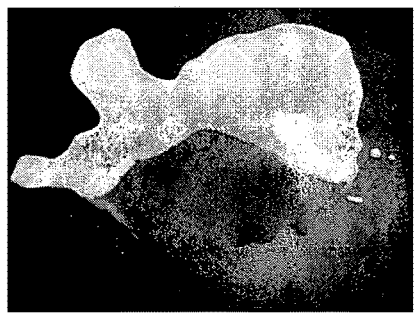
FIG. 15 shows the appearance of a suspension obtained by sifting a spray-freeze-dried product to collect a powder obtained between sieves of 75 μm and 250 μm and dispersing the powder in water.
Figure 16:
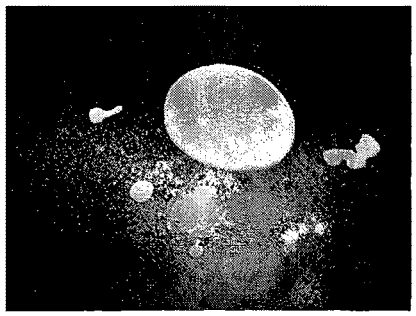
FIG. 16 shows the appearance of a suspension obtained by sifting a spray-freeze-dried product to collect a powder that passed through a sieve of 75 μm and dispersing the powder in water.

The powder obtained by sifting the spray-freeze-dried product and collected between the sieves of 75 μm and 250 μm was also easily redispersed without problems, and no agglomerates were observed in the suspension removed from the vial (FIG. 15). However, the powder that passed through the sieve of 75 μm was not completely redispersed and some remained in a powder state (FIG. 16).

Figure 17:
FIG. 17 shows the appearance of a suspension obtained by crushing a vial-freeze-dried product in a vial, sifting the powder to collect a powder that passed through a sieve of 75 μm, and dispersing the powder in water.
Figure 18:
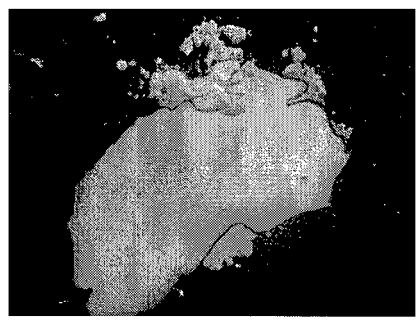
FIG. 18 shows the appearance of a suspension obtained by crushing a vial-freeze-dried product in the vial, sifting the powder to collect a powder obtained between sieves of 75 μm and 250 μm, and dispersing the powder in water.

The powder obtained by crushing the vial-freeze-dried product in the vial and sifting was not easily redispersed and some of the powder remained in a powder state, whether the powder particles passed through the sieve of 75 mm or were collected between the sieve of 75 mm and 250 mm (FIG. 17: powder of less than 75 mm, FIG. 18: powder of 75 mm to 250 mm).

The above results indicated that the powder obtained by crushing a vial-freeze-dried product exhibits poor dispersibility in water, irrespective of the particle size, and that the powder obtained by spray-freeze-drying the suspension exhibits good dispersibility in water when the particles have a diameter larger than a certain level. In the field of freeze-drying, it is thought that as freezing speed increases and the volume of liquid to be frozen decreases, smaller ice crystals are formed, which inhibits agglomeration of particles (see, for example, Journal of Pharmaceutical Sciences, Vol. 92, No. 2, 319-332 (2003)). Therefore, in spray-freeze-drying that enables quick freeze-drying of small droplets, it is predicted that as the size of the obtained particles is smaller, agglomeration of particles is more effectively inhibited. Therefore, the obtained results were unexpected.

In the powder obtained by spray-freeze-drying, small particles were scarcely present. Therefore, sifting to remove the particles with a small particle size is not particularly necessary, and the obtained powder exhibited practical dispersibility even without sifting (i.e., the powder exhibited good dispersibility and a homogeneous suspension was obtained).

The invention claimed is:

1. A freeze-dried aripiprazole formulation obtained by a process comprising the steps of spray-freezing an aripiprazole suspension comprising
   (I) aripiprazole,
   (II) a vehicle for the aripiprazole, and
   (III) water for injection;
      drying,
      sifting through a sieve,
   wherein the freeze-dried formulation consists essentially of particles not passing through a sieve having an opening size of 75 µm and passing through a sieve having an opening size of 1000 µm.

2. The freeze-dried formulation according to claim 1, wherein the aripiprazole is present in an amount of 50 w/w % or more.

3. The freeze-dried formulation according to claim 1, which has a bulk density of about 0.05 to about 0.5 g/m L.

4. The freeze-dried formulation according to claim 1, wherein the aripiprazole has a mean particle size of about 1 to about 10 microns.

5. The freeze-dried formulation according to claim 4, wherein the aripiprazole has a mean particle size of about 2.5 microns.

6. The freeze-dried formulation according to claim 1, wherein the vehicle is at least one member selected from the group consisting of suspending agents, bulking agents, and buffers.

7. The freeze-dried formulation according to claim 1, wherein the vehicle comprises
   (II-a) one or more suspending agents,
   (II-b) one or more bulking agents, and
   (II-c) one or more buffers.

8. The freeze-dried formulation according to claim 1, wherein the vehicle comprises
   (II-a) carboxymethyl cellulose or a salt thereof,
   (II-b) mannitol, and
   (II-c) sodium phosphate.

9. The freeze-dried formulation according to claim 1, further comprising (IV) a pH adjusting agent.

10. The freeze-dried formulation according to claim 9, wherein the pH adjusting agent is sodium hydroxide.

11. The freeze-dried formulation according to claim 9, comprising
    (I) aripiprazole,
    (II-a) carboxymethyl cellulose or a sodium salt thereof,
    (II-b) mannitol,
    (II-c) sodium phosphate, and optionally
    (IV) sodium hydroxide.

12. The freeze-dried formulation according to claim 1, wherein the aripiprazole is in a monohydrate form.

13. A process for producing a freeze-dried aripiprazole formulation comprising the steps of
    spray-freezing an aripiprazole suspension having a mean particle size in the range of about 1 to about 10 microns to obtain spray-frozen particles;
    drying the spray-frozen particles to obtain spray-freeze-dried particles, and
    selecting particles not passing through a sieve having an opening size of 75 µm and passing through a sieve having an opening size of 1000 µm by sifting through a sieve.

14. A process for producing a freeze-dried aripiprazole formulation, comprising the steps of
    reducing the mean particle size of aripiprazole in a sterile primary suspension formed by mixing aripiprazole, a vehicle for the aripiprazole, and water to the range of about 1 to about 10 microns to form a final suspension;
    spray-freezing the aripiprazole suspension having a mean particle size of about 1 to about 10 microns to obtain spray-frozen particles; and
    drying the spray-frozen particles to obtain spray-freeze-dried particles, and selecting particles not passing through a sieve having an opening size of 75 µm and passing through a sieve having an opening size of 1000 µm by sifting through a sieve.

15. The process according to claim 14, wherein the reduction of the mean particle size of aripiprazole in the sterile primary suspension is carried out by wet milling.

16. The process according to claim 13, wherein the spray-freezing is carried out by either spraying at a low temperature for freezing or spraying under reduced pressure for freezing.

17. The freeze-dried formulation according to claim 1, which exhibits good dispersibility and forms a homogenous aripiprazole suspension upon reconstitution with water.

18. The freeze-dried formulation according to claim 1, comprising particles passing through a sieve having an opening size of 75 µm in an amount of 15 w/w % or less.

19. The process according to claim 14, wherein the spray-freezing is carried out by either spraying at a low temperature for freezing or spraying under reduced pressure for freezing.

* * * * *